US00PP25587P2

(12) United States Plant Patent
Bernuetz

(10) Patent No.: US PP25,587 P2
(45) Date of Patent: May 26, 2015

(54) *EUPHORBIA* PLANT NAMED 'BONPRI 515'

(50) Latin Name: ***Euphorbia pulcherrima* Willd. ex *Klotzsch*×*Euphorbia cornastra***
Varietal Denomination: Bonpri 515

(71) Applicant: Andrew Bernuetz, Silverdale (AU)

(72) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 150 days.

(21) Appl. No.: 13/986,549

(22) Filed: May 14, 2013

(51) Int. Cl.
*A01H 5/00* (2006.01)

(52) U.S. Cl.
USPC ..... Plt./302

(58) Field of Classification Search
USPC ..... Plt./302
See application file for complete search history.

*Primary Examiner* — Susan McCormick Ewoldt
(74) *Attorney, Agent, or Firm* — C. A. Whealy

(57) ABSTRACT

A new and distinct cultivar of *Euphorbia* plant named 'Bonpri 515', characterized by its upright and mounded plant habit; vigorous growth habit; freely branching habit; dark green-colored leaves; inflorescences with multiple bright red purple-colored flower bracts; relatively small cyathia; and good post-production longevity.

1 Drawing Sheet

Botanical designation: *Euphorbia pulcherrima* Willd. ex *Klotzsch*×*Euphorbia cornastra.*

Cultivar denomination: 'BONPRI 515'.

BACKGROUND OF THE INVENTION

The present invention relates to a new and distinct cultivar of *Euphorbia* plant, an interspecific hybrid botanically known as *Euphorbia pulcherrima* Willd. ex *Klotzsch*×*Euphorbia cornastra*, and hereinafter referred to by the name 'Bonpri 515'.

The new *Euphorbia* plant is a product of a planned breeding program conducted by the Inventor in Yellow Rock, New South Wales, Australia. The objective of the program is to create and develop new interspecific *Euphorbia* plants with upright and mounded plant habit and multiple bright red purple-colored flower bracts per inflorescence.

The new *Euphorbia* plant originated from a cross-pollination by the Inventor in June, 2005 of a proprietary selection of *Euphorbia pulcherrima* Willd. ex *Klotzsch* identified as code number 392, not patented, as the female, or seed, parent with an unidentified proprietary selection of *Euphorbia cornastra*, not patented, as the male, or pollen, parent. The new *Euphorbia* plant was discovered and selected by the Inventor as a single flowering plant within the progeny of the stated cross-pollination in a controlled greenhouse environment in Yellow Rock, New South Wales, Australia in November, 2006.

Asexual reproduction of the new *Euphorbia* plant by terminal vegetative cuttings in a controlled greenhouse environment in Yellow Rock, New South Wales, Australia since November, 2006 has shown that the unique features of this new *Euphorbia* plant are stable and reproduced true to type in successive generations of asexual reproduction.

SUMMARY OF THE INVENTION

Plants of the new *Euphorbia* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpri 515'. These characteristics in combination distinguish 'Bonpri 515' as a new and distinct *Euphorbia* plant:

1. Upright and mounded plant habit.
2. Vigorous growth habit.
3. Freely branching habit.
4. Dark green-colored leaves.
5. Inflorescences with multiple bright red purple-colored flower bracts.
6. Relatively small cyathia.
7. Good post-production longevity.

In side-by-side comparisons conducted in Yellow Rock, New South Wales, Australia, plants of the new *Euphorbia* differ primarily from plants of the female parent selection in the following characteristics:

1. Plants of the new *Euphorbia* are more compact than plants of the female parent selection.
2. Plants of the new *Euphorbia* and the female parent selection differ in flower bract color as plants of the female parent selection have speckled pink-colored flower bracts.

In side-by-side comparisons conducted in Yellow Rock, New South Wales, Australia, plants of the new *Euphorbia* differ primarily from plants of the male parent selection in the following characteristics:

1. Plants of the new *Euphorbia* are more compact than plants of the male parent selection.
2. Plants of the new *Euphorbia* and the male parent selection differ in flower bract color as plants of the male parent selection have pink-colored flower bracts.

Plants of the new *Euphorbia* can be compared to plants of the *Euphorbia pulcherrima*×*Euphorbia cornastra* 'Eckcory', disclosed in U.S. Plant Pat. No. 15,849. In side-by-side comparisons conducted in Yellow Rock, New South Wales, Australia, plants of the new *Euphorbia* differed from plants of 'Eckcory' in the following characteristics:

1. Plants of the new *Euphorbia* were larger and more vigorous than plants of 'Eckcory'.
2. Plants of the new *Euphorbia* had thicker lateral branches than plants of 'Eckcory'.
3. Plants of the new *Euphorbia* larger leaves than plants of 'Eckcory'.
4. Plants of the new *Euphorbia* had larger inflorescences with larger flower bracts than plants of 'Eckcory'.
5. Inflorescences of plants of the new *Euphorbia* had about four times as many flower bracts as inflorescences of plants of 'Eckcory'.
6. Flower bracts of plants of the new *Euphorbia* were more upright than flower bracts of plants of 'Eckcory'.
7. Flower bracts of plants of the new *Euphorbia* and 'Eckcory' differed slightly in color.
8. Plants of the new *Euphorbia* had smaller cyathia than plants of 'Eckcory'.
9. Plants of the new *Euphorbia* had shorter flower bract petioles than plants of 'Eckcory'.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the sheet comprises a side perspective view of a typical flowering plant of 'Bonpri 515' grown in a container.

The photograph at the bottom of the sheet is a close-up view of a typical inflorescence of 'Bonpri 515'.

DETAILED BOTANICAL DESCRIPTION

Plants used in the aforementioned photographs and herewith described in detail were grown in 12-cm containers during the autumn in an outdoor nursery in Higashiomi, Shiga, Japan and under cultural practices typical of commercial *Euphorbia* production. During the production of the plants, day temperatures averaged 23° C. and night temperatures averaged 13° C. Plants were pinched one time and were four months old when the photographs and the description were taken. In the following description, color references are made to The Royal Horticultural Society Colour Chart, Fourth Edition, 2007, except where general terms of ordinary dictionary significance are used.

Botanical classification: *Euphorbia pulcherrima* Willd. ex *Klotzsch*×*Euphorbia cornastra* 'Bonpri 515'.

Parentage:

*Female, or seed, parent*.—Proprietary selection of *Euphorbia pulcherrima* Willd. ex *Klotzsch* identified as code number 392, not patented.

*Male, or pollen, parent*.—Unidentified proprietary selection of *Euphorbia cornastra*, not patented.

Propagation:

*Type*.—Terminal vegetative cuttings.

*Time to initiate roots, summer*.—About seven days at 20° C. to 25° C.

*Time to initiate roots, winter*.—About nine days at 20° C. to 22° C.

*Time to produce a rooted young plant, summer*.—About three weeks at 20° C. to 25° C.

*Time to produce a rooted young plant, winter*.—About four weeks at 20° C. to 22° C.

*Root description*.—Fibrous; white in color.

*Rooting habit*.—Freely branching; medium density.

Plant description:

*Plant habit and form*.—Upright and mounded plant habit; inverted triangle; inflorescences positioned above the foliar plane; vigorous growth habit.

*Plant height*.—About 25.8 cm.

*Plant diameter or spread*.—About 33.1 cm.

*Lateral branch description*.—Branching habit: Freely branching habit, about three to four lateral branches develop per plant; pinching enhances lateral branch development. Length: About 16.6 cm. Diameter: About 6.2 mm. Internode length: About 2.6 cm. Aspect: Mostly upright. Strength: Strong. Texture: Smooth, glabrous. Color: Close to 146A.

*Leaf description*.—Arrangement: Alternate, simple. Length: About 11 cm. Width: About 7.4 cm. Shape: Ovate. Apex: Acute. Base: Rounded. Margin: Shallowly serrulate. Venation pattern: Pinnate, reticulate. Texture, upper and lower surfaces: Pubescent. Color: Developing leaves, upper surface: Close to 143A. Developing leaves, lower surface: Close to 144A. Fully developed leaves, upper surface: Close to N137A; venation, close to 145B. Fully developed leaves, lower surface: Close to 137C; venation, close to 145B. Petioles: Length: About 3.9 cm. Diameter: About 2.4 mm. Texture, upper and lower surfaces: Sparsely pubescent. Color, upper and lower surfaces: Close to 145B.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—One inflorescence develops per lateral branch.

*Inflorescence diameter*.—About 17 cm.

*Inflorescence height*.—About 6.3 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering habit, plants flower about 50 days under natural season conditions in Japan.

*Post-production longevity*.—Good post-production longevity; plants of the new Euphorbia maintain good substance and bract color for about six weeks.

*Flower bracts*.—Quantity per inflorescence: Numerous, about 35. Length, largest bracts: About 9.1 cm. Width, largest bracts: About 5.3 cm. Shape: Ovate to lanceolate. Apex: Cuspidate. Base: Rounded. Margin: Entire to shallowly serrulate. Texture, upper and lower surfaces: Smooth, glabrous. Aspect: Semi-upright to horizontal. Venation pattern: Pinnate, reticulate. Color: Transitional bracts, upper surface: Close to 138B and N57B; towards the margins, close to 165A. Transitional bracts, lower surface: Close to NN155A and 70C; towards the margins, close to 138A to 138B. Fully expanded bracts, immature, upper surface: Close to 53B. Fully expanded bracts, immature, lower surface: Close to 53D. Fully expanded bracts, mature, upper surface: Close to 58B;

venation, close to 58A to 58B. Fully expanded bracts, mature, lower surface: Close to 67D; venation, close to 145C. Flower bract petioles: Length: About 8.1 mm. Diameter: About 1.7 mm. Texture, upper and lower surfaces: Smooth, glabrous. Color, upper surface: Close to N57B. Color, lower surface: Close to 145A.

*Cyathia*.—Quantity per corymb: About 30. Diameter of cyathia cluster: About 4 cm. Height, individual cyathium: About 2.4 mm. Diameter, individual cyathium: About 1.6 mm. Shape, individual cyathium: Globose; sessile. Color: Close to 144C. Nectaries: Nectary development has not been observed on plants of the new *Euphorbia*.

*Reproductive organs*.—Reproductive organ development has not been observed on plants of the new *Euphorbia*.

*Seeds and fruits*.—Seed and fruit production has not been observed on plants of the new *Euphorbia*.

Disease & pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpri 515' as illustrated and described.

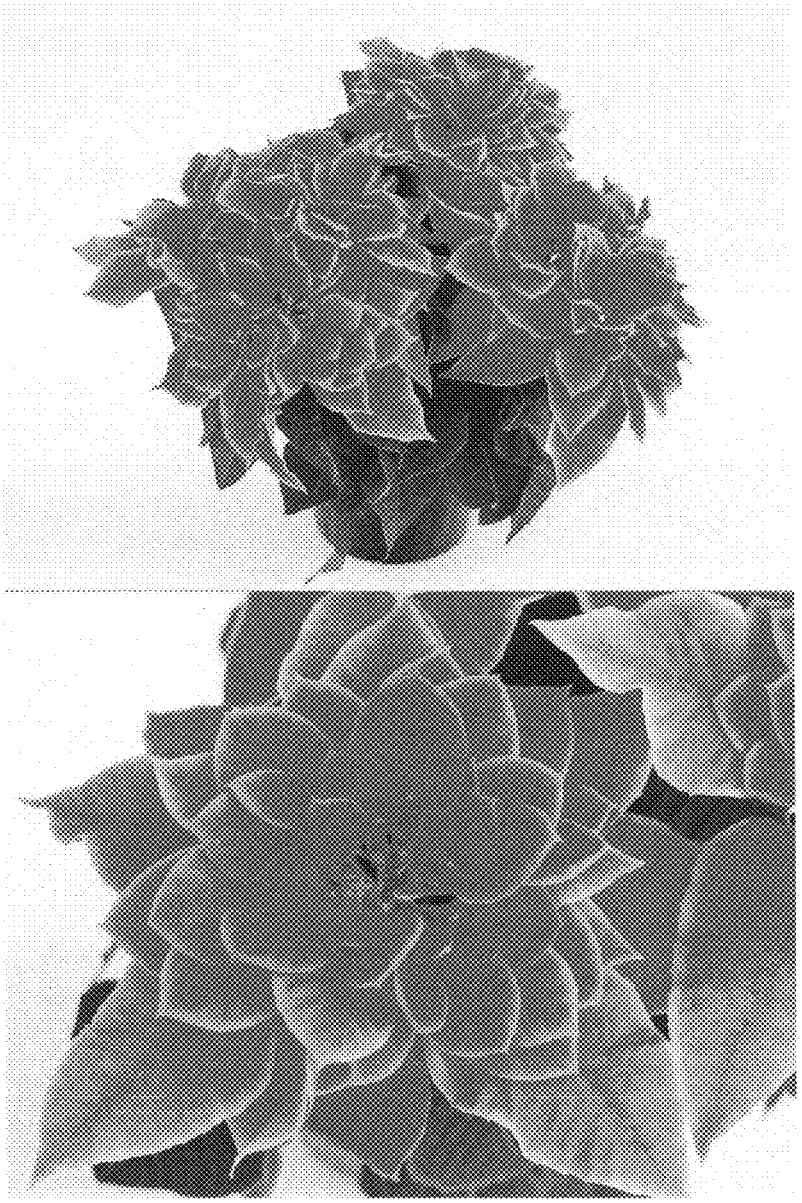

* * * * *